US011191605B2

(12) United States Patent
Dejardin et al.

(10) Patent No.: US 11,191,605 B2
(45) Date of Patent: Dec. 7, 2021

(54) INGRESS-EGRESS APPARATUS FOR PROTECTION OF SURGICAL FIELD DURING REMOVAL OF SURGICAL IMPLANTS, AND RELATED METHODS

(71) Applicant: BOARD OF TRUSTEES OF MICHIGAN STATE UNIVERSITY, East Lansing, MI (US)

(72) Inventors: Loic M. Dejardin, East Lansing, MI (US); Kyle A. Snowdon, Akron, OH (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 77 days.

(21) Appl. No.: 16/351,672

(22) Filed: Mar. 13, 2019

(65) Prior Publication Data
US 2019/0282319 A1  Sep. 19, 2019

Related U.S. Application Data

(60) Provisional application No. 62/642,284, filed on Mar. 13, 2018.

(51) Int. Cl.
*A61B 90/00* (2016.01)
*A61B 17/92* (2006.01)
(Continued)

(52) U.S. Cl.
CPC .............. *A61B 90/03* (2016.02); *A61B 17/92* (2013.01); *A61B 17/17* (2013.01);
(Continued)

(58) Field of Classification Search
CPC ....... A61B 17/02; A61B 17/92; A61B 17/921; A61B 17/17; A61B 17/1735; A61B 17/88;
(Continued)

(56) References Cited

U.S. PATENT DOCUMENTS 3,936,213 A * 2/1976 Kappel .............. B23Q 11/0053
408/67
5,762,606 A * 6/1998 Minnich ............ A61B 17/0231
600/201

(Continued)

OTHER PUBLICATIONS

Loic Dejardin, "To Nail or Not to Nail", presented at Veterinary Orthopedic Society (VOS) 2017 Conference (Snowbird, UT) on Mar. 15, 2017 (44 pages).

*Primary Examiner* — Matthew J Lawson
(74) *Attorney, Agent, or Firm* — Marshall, Gerstein & Borun LLP

(57) ABSTRACT

An ingress-egress apparatus for protection of a surgical work site during removal of a surgical implant therefrom includes an inverted frustum surface having a sidewall defining: a bottom open area at a base portion of the frustum surface sidewall, and an opposing top open area at a top portion of the frustum surface sidewall. The top open area has a larger area than the bottom open area. The apparatus includes an ingress port located at the base portion of the frustum surface sidewall and an egress port located at the base portion of the frustum surface sidewall. During surgical removal of the surgical implant using a surgical burr, the apparatus can be used to irrigate the work site, thereby cooling it and protecting it from damage, and further removing metal implant particles generated during burring.

18 Claims, 3 Drawing Sheets

(51) Int. Cl.
*A61B 17/56* (2006.01)
*A61B 17/17* (2006.01)
*A61B 17/00* (2006.01)

(52) U.S. Cl.
CPC ............ *A61B 2017/0042* (2013.01); *A61B 2017/564* (2013.01); *A61B 2090/036* (2016.02); *A61B 2090/08021* (2016.02); *A61B 2217/005* (2013.01); *A61B 2217/007* (2013.01)

(58) Field of Classification Search
CPC ............ A61B 90/02; A61B 90/03; A61B 2017/0212; A61B 2017/0231; A61B 17/3468; A61B 17/3423; A61B 17/3441; A61B 17/025; A61B 17/0231; A61B 17/0218
See application file for complete search history.

(56) References Cited

U.S. PATENT DOCUMENTS

| | | | | |
|---|---|---|---|---|
| 5,971,977 | A * | 10/1999 | Korenfeld | A61B 17/0231 606/1 |
| 6,071,295 | A * | 6/2000 | Takahashi | A61B 17/02 604/176 |
| 6,267,752 | B1 * | 7/2001 | Svetliza | A61B 3/0008 600/205 |
| 2004/0210229 | A1 * | 10/2004 | Meller | A61B 10/025 606/80 |
| 2009/0012370 | A1 * | 1/2009 | Gutierrez | A61B 17/02 600/201 |
| 2010/0298835 | A1 * | 11/2010 | Ralph | A61B 17/17 606/80 |
| 2015/0011938 | A1 * | 1/2015 | Gill | A61B 17/3415 604/151 |
| 2015/0141964 | A1 * | 5/2015 | MacMillan | A61B 17/707 604/522 |
| 2018/0161024 | A1 * | 6/2018 | Davis | A61B 1/313 |
| 2019/0142407 | A1 * | 5/2019 | Jung | A61B 17/1617 600/104 |
| 2021/0000501 | A1 * | 1/2021 | Coe | A61B 17/0293 |
| 2021/0219994 | A1 * | 7/2021 | Muller | A61B 1/00066 |

* cited by examiner

INGRESS-EGRESS APPARATUS FOR PROTECTION OF SURGICAL FIELD DURING REMOVAL OF SURGICAL IMPLANTS, AND RELATED METHODS

CROSS REFERENCE TO RELATED APPLICATION

Priority is claimed to U.S. Provisional Application No. 62/642,284 (filed Mar. 13, 2018), which is incorporated herein by reference in its entirety.

STATEMENT OF GOVERNMENT INTEREST

None.

BACKGROUND OF THE DISCLOSURE

Field of the Disclosure

The disclosure relates to an ingress-egress apparatus and related for protection of a surgical work site during removal of a surgical implant therefrom.

Background

During many types of surgery, surgical implants are regularly used to stabilize the repaired area. These surgical implants include screws, bolts, prostheses, TTA (tibial tuberosity advancement) cages can be extremely difficult to remove if they are partially damages or have become embedded in the bone. In these cases, in an attempt to preserve the surrounding tissue, the best course of action can be to the burr the implant out via use of high speed surgical burrs. Surgical burring generates heat which can damage soft tissue. Also, surgical burring releases large amounts of metal particles into the soft tissues and if near joints, these particles can lead to discomfort. To reduce heat and the release of the metal particles into the surrounding tissues, copious continuous saline irrigation is often used. Unfortunately, the irrigation can contribute to soft tissue swelling, carrying metal particles deeper into the tissue, and cause postsurgical infection risk. There currently does not exist an efficient means to remove these small metal fragments generated during surgery.

SUMMARY

In an aspect, the disclosure relates to an ingress-egress apparatus for protection of a surgical work site during removal of a surgical implant therefrom, the apparatus comprising: an inverted frustum surface comprising a sidewall defining: a bottom open area at a base portion of the frustum surface sidewall, and an opposing top open area at a top portion of the frustum surface sidewall, wherein the top open area has a larger (cross-sectional) area than the bottom open area; an ingress (or inlet) port located at the base portion of the frustum surface sidewall and providing fluid communication access from (i) external to the ingress-egress apparatus to (ii) the bottom open area; and an egress (or outlet) port located at the base portion of the frustum surface sidewall and providing fluid communication access from (i) external to the ingress-egress apparatus to (ii) the bottom open area.

In another aspect, the disclosure relates to a method for removing a surgical implant, the method comprising: providing a surgical subject (or patient) comprising an (internal) surgical implant to be removed; burring the surgical implant with a surgical burr to remove the surgical implant, wherein burring the surgical implant comprises: providing surgical access to the surgical implant with an ingress-egress apparatus according to any of the variously disclosed embodiments, accessing the surgical implant with the surgical burr through the bottom open area of the ingress-egress apparatus while burring the implant, iirrigating the surgical implant with water delivered through the ingress port of the ingress-egress apparatus, thereby forming a wash fluid comprising the water and burring residue, and removing the wash fluid through the egress port of the ingress-egress apparatus.

BRIEF DESCRIPTION OF THE DRAWINGS

For a more complete understanding of the disclosure, reference should be made to the following detailed description and accompanying drawings wherein.

While the disclosed apparatus, compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

DETAILED DESCRIPTION

The disclosure relates to an ingress-egress device, which greatly improves cleaning and removing of metal fragments during surgical burring. This device includes structure for continuous input (via an ingress port) and removal (via an egress port) of a sterile saline solution to irrigate a surgical work site during removal of a surgical implant with a surgical burr. A vortex forms at the end of the device which helps remove metal particles during surgical burring. Specifically, swirling, vortex flow of irrigating water in a circular base of the device suspends dispersed metal particles, whereupon the metal particles migrate radially outward (e.g., toward the device sidewall at its circular base) and can be removed from the surgical work site via the egress port at the device sidewall. This device also keeps the area cool during the burring procedure. Lastly, it is more sanitary than directly flooding the area with a saline solution, which can become contaminated and then fall back into the wound. This device ensures the rapid removal of any saline solution exposed to the wound, and therefore greatly improves the probability that no post-surgical infection will occur.

Figure 1:
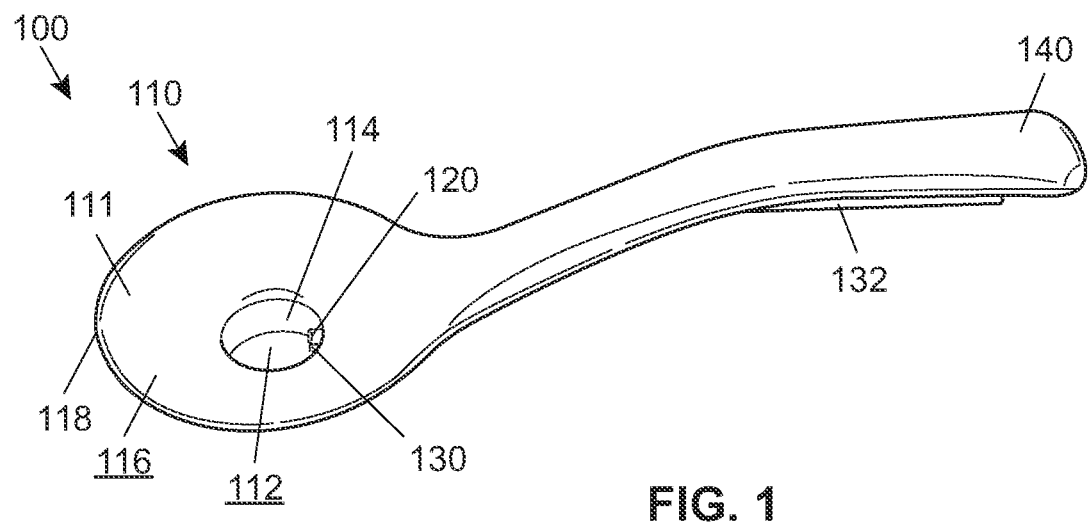
FIG. 1 illustrates a top perspective view of an ingress-egress device according to the disclosure.
Figure 2:
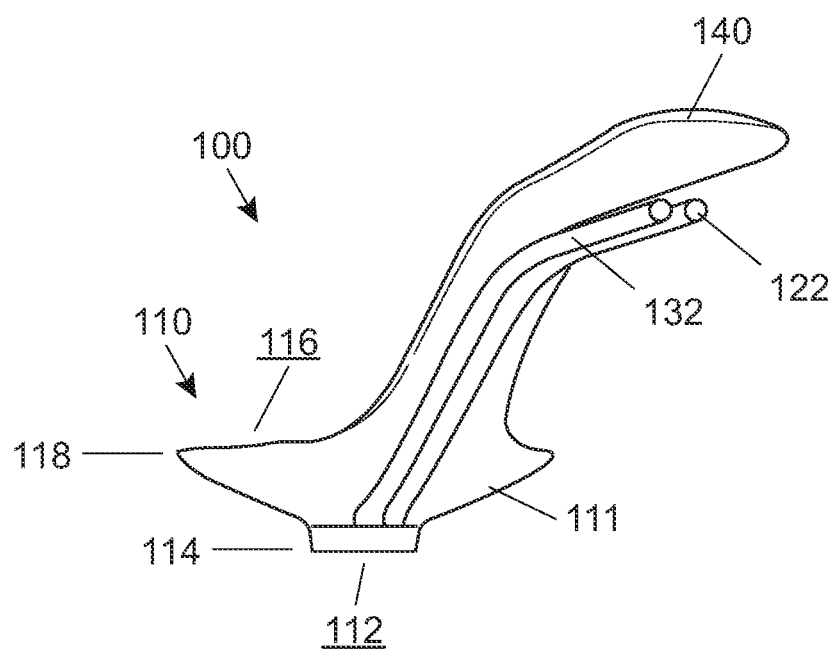
FIG. 2 illustrates a back perspective view of an ingress-egress device according to the disclosure, particularly showing inlet/outlet lines to the corresponding ingress/egress ports.
Figure 3:
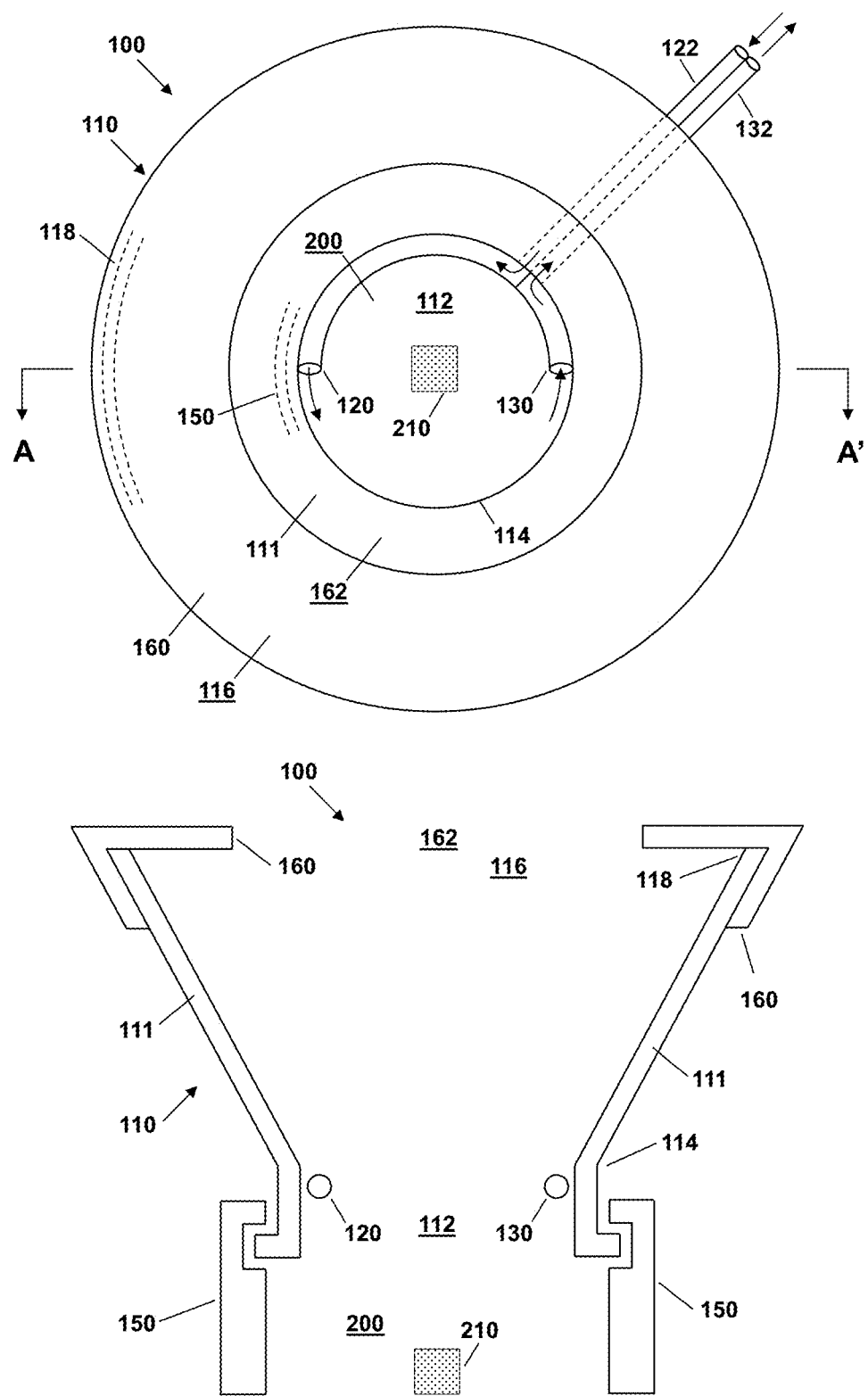
FIG. 3 illustrates a top view (top) and a side cross-section (bottom; view A-A' from top view) of an ingress-egress device according to the disclosure, particularly showing optional soft base and soft awning components.
Figure 4:
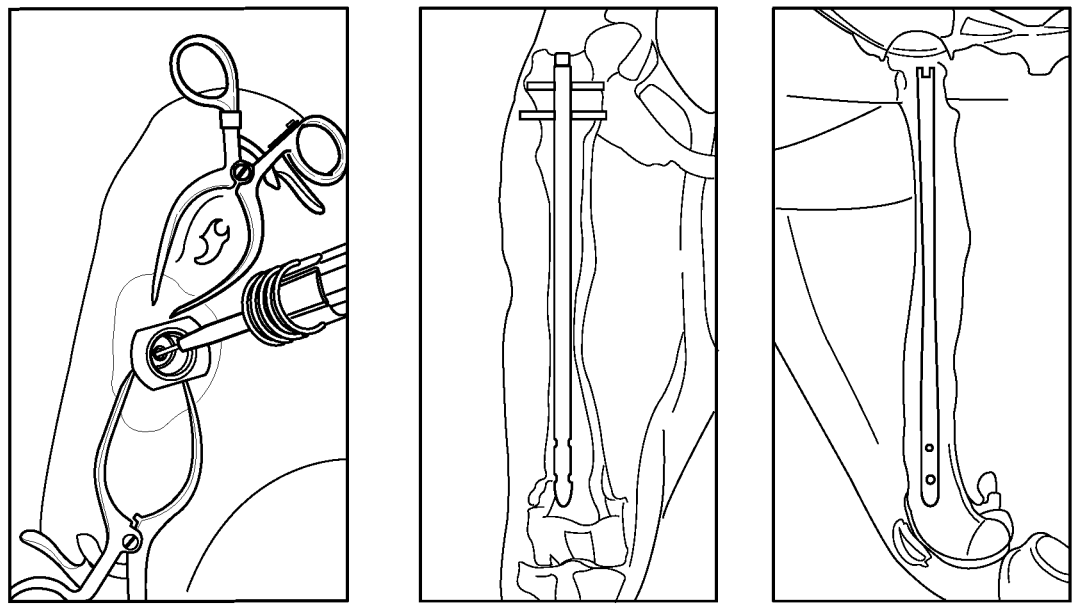
FIG. 4 illustrates a surgical method for removal of a surgical implant using a surgical burr. The left image illustrates a plate screw with a damaged coupling being removed using a surgical high speed burr. A syringe casing is used to contained irrigation fluid contaminated with metal particles. The center and right images are radiographs of a healed femoral fracture treated with an I-LOC nail. The driving shaft of the most distal bolt had fractured during removal. The remnant of the locking bolt was removed using the same technique. The nail cannulation had a larger diameter as a result of burring.
Figure 5:
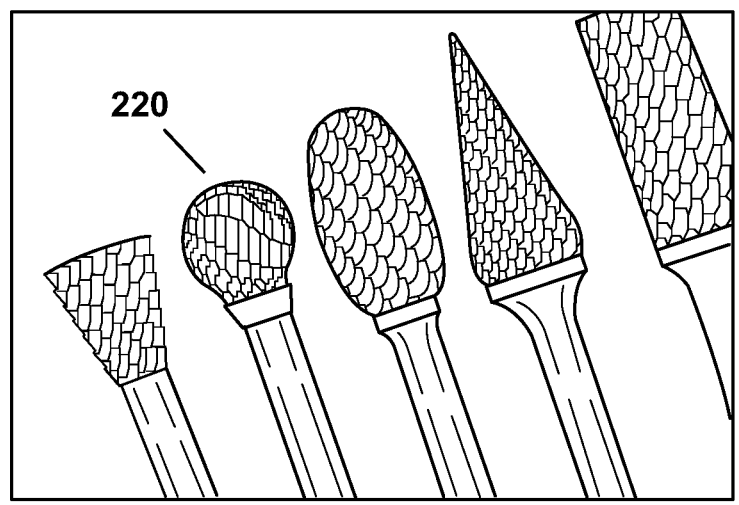
FIG. 5 illustrates surgical burrs for use with an ingress-egress device according to the disclosure when removing surgical implants.

FIGS. 1-3 illustrate an ingress-egress device 100 according to the disclosure. The device has a funnel shape 110 that can include several structural features: ingress and egress ports 120, 130, a handle 140 (e.g., for a user to hold the device 100 while shielding inlet/outlet lines 122, 132), a conforming soft base 150 to prevent contaminated fluid from leaking into surrounding tissues, and a soft awning (or skirt) 160 to limit splatter while providing unrestricted surgical burr 210 access to the surgical work site 200 and the surgical implant 210.

In an aspect, the disclosure relates to an ingress-egress apparatus 100 for protection of a surgical work site 200 during removal of a surgical implant 210 therefrom. The apparatus 100 generally includes an inverted frustum surface 110 having a sidewall 111. The frustum surface 110 and sidewall 111 define a bottom open area 112 (e.g., having a width or diameter of at least 0.5 or 1 cm and/or up to 1.5, 2, or 3 cm; circular area) at a base portion 114 of the frustum surface 110 sidewall 111, and an opposing top open area 116 (e.g., having a width or diameter of at least 2, 3, or 4 cm and/or up to 4, 6, 8, or 10 cm; circular area) at a top portion 118 of the frustum surface 110 sidewall 111. The top open area 116 can have a larger (cross-sectional) area than the bottom open area 112 (e.g., as illustrated). The apparatus 100 further includes an ingress (or inlet) port 120 located at the base portion 114 of the frustum surface 110 sidewall 111, which port 120 provides fluid communication access from (i) a region external to the ingress-egress apparatus 100 to (ii) the bottom open area 112 (e.g., and neighboring internal volume of the ingress-egress apparatus 100 and the surgical work site/implant site 200 where being used for implant 210 removal). The apparatus 100 further includes an egress (or inlet) port 130 located at the base portion 114 of the frustum surface 110 sidewall 111, which port 120 also provides fluid communication access from (i) a region external to the ingress-egress apparatus 100 to (ii) the bottom open area 112 (e.g., and neighboring internal volume of the ingress-egress apparatus 100 and the surgical work site/implant site 200 where being used for implant 210 removal). The frustum surface 110 can generally be a funnel shape or a frustoconical shape. The sidewalls 111 of the frustum 110 are generally outwardly sloping in an upward direction. The sidewalls 111 can be substantially straight as in the illustrated embodiments, or they can be sloped or curved, such as having an upper/top concave surface and a lower/bottom convex surface. The apparatus 100 and its components can be formed from any suitable material, for example metal (e.g., surgical stainless steel), a rigid plastic material, etc.

The apparatus 100 can further include an inlet line 122 in fluid communication with the ingress port 120, for example as tubing connected to the ingress port 102 at one end and connected to (or adapted to be connected to) a source of irrigating fluid (not shown), such as water, saline solution, etc. The apparatus 100 can further include an outlet line 132 in fluid communication with the egress port 130, for example as tubing connected to the egress port 130 at one end and connected to (or adapted to be connected to) a suction source (not shown) for evacuating wash/irrigation fluid from the surgical work site 200.

In an embodiment, the ingress port 120 and the egress port 130 are spaced apart at an interior location of the bottom open area 112. The ingress/egress ports 120/130 can be spaced apart on opposing sides of the base portion 114 sidewall 111, for example at 90°-270°, at 135°-225°, or at about 180° from each other in a circular base. Spacing apart allows irrigating water/fluid to enter the bottom open area from the ingress port 120, irrigate the surgical work site 200 as water flows across the site to cool the site and pick up particulate implant metal, and then be removed from the work site/bottom open area via the egress port 130. Preferably, a circular base portion/bottom open area induces a vortex swirling flow therein to assist in metal particulate pick-up and removal at the egress port sidewall via centrifugal or cyclonic separation. In an embodiment, the inlet/outlet lines 122/132 can enter or pass through the sidewall 111 on/at the same side or relative location of the sidewall, and then one or both of the lines can curve or wrap around the bottom open area interior before having their exit orifice open into the interior of the apparatus 100. This allows convenient wash water inlet/suction outlet at the same external physical location of the apparatus 100, but still allows internal cross flow and/or vortex flow in the water flow path around the surgical work site 200.

The apparatus 100 can further include a conforming soft base 150 (e.g., rubber or other soft/flexible sealing material) attached to the inverted frustum surface 110 at the base portion 114 and around the bottom open area 112. The base 150 can be a circular or cylindrical attachment, such as having a width or diameter of at least 0.5 or 1 cm and/or up to 1.5, 2, or 3 cm. The base 150 can fit or attach over an outer circumferential lip of an outer base portion 114 of the sidewall 111.

The apparatus 100 can further include a soft awning 160 (or skirt; rubber, fabric, or other soft/flexible covering material) cover attached to the inverted frustum surface 110 at the top portion 118 and around the top open area 116. The awning 160 includes an interior opening 162 (e.g., sized for surgical burr 220 access). The interior opening 162 of the awning or skirt can be sized similar to the bottom open area 112, such as having a width or circular diameter of at least 0.5 or 1 cm and/or up to 1.5, 2, or 3 cm. The interior opening 162 of the awning or skirt 160 provides access to the surgical site 200 with the surgical burr 220, but limits back-splatter out of the surgical work site 200 and out of the top of the apparatus 100. Back-splatter stopped by the cover of the awning or skirt 160 can fall back down (e.g., along the internal surface of the sidewall 111) into the bottom open area 112 where it can be recovered and evacuated via the egress port 130. The flexible or soft material for the awning 160 allows the surgeon to bend or stretch the awning material if needed to access the surgical work site 200 at an angle with the surgical burr/surgical drill.

In another aspect, the disclosure relates to a method for removing a surgical implant 210. The method is generally performed on a surgical subject (or patient) having an (internal) surgical implant 210 to be removed. The method includes burring the surgical implant 210 with a surgical burr 220 to remove the surgical implant 210. The surgical burr 220 can be a cutting, shaving, and/or filing burr with a contoured or toothed distal tip that can be used for cutting, shaving, and/or filing the surgical implant 210 for removal. The surgical burr 220 can be attached to or a component of a surgical drill (not shown). Burring the surgical implant 210 can include several steps as described. After burring or removal of the implant 210, further surgical procedures can include removing the surgical burr 220, removing the apparatus 100, closing the wound at the incision point, etc.

Surgical access is provided to the surgical implant 210 with the ingress-egress apparatus 100 accord to any of its various embodiments. Providing surgical access to the surgical implant can include making a surgical opening (or incision) at a surgical work site 200 where the surgical implant 210 is located in the surgical subject, and then inserting a bottom portion of the apparatus 100 into the surgical subject at the surgical work site 200 and positioned above the surgical implant 210. The bottom portion of the ingress-egress apparatus 100 could be the base portion 114 of the frustum 110, or it could be the conforming soft base 150 when present, for example.

The surgical implant 210 is accessed and burred with the surgical burr 220 (e.g., the distal tip thereof) through the bottom open area 112 of the apparatus 100 while burring the implant 210. In an embodiment, burring the surgical implant 210 is performed to partially remove the implant 210. For example, a portion of the implant 210 could be outside the desired implant area within the subject or patient, broken, and/or damaged, but another portion of the implant 210 could be inserted properly and functioning as desired. Accordingly, the method can be used to partially remove the undesired portion of the surgical implant 210 while leaving the desired portion of the implant 210 in place within the subject. In another embodiment, burring the surgical implant 210 is performed to completely remove the surgical implant 210. For example, the implant 210 could be no longer needed (e.g., it has served its purpose and should be removed from the subject). Alternatively, the implant 210 could have been damaged or otherwise needs to be removed, for example for possible replacement.

The surgical implant 210 (e.g., and the surrounding surgical work site 200) is irrigated with water (e.g., water-containing solution or mixture such as a saline solution) during burring. The water is delivered through the ingress port 120 of the apparatus 100, thereby forming a wash fluid including the fresh inlet water or water solution and burring residue. The burring residue can include metal or other implant material particles or fragments, and can possibly include particles or fragments of released bone or other body tissue. Similarly, the wash fluid is removed during burring through the egress port 130 of the apparatus 100.

In an embodiment, irrigating the surgical implant 210 with water includes injecting the water through the ingress port 120 under pressure to attain a desired wash flow rate and velocity. Alternatively or additionally, removing the wash fluid can include applying suction through the egress port 130. The inlet and outlet flow rates of (fresh) water and wash water, respectively, are preferably balanced or otherwise selected so that the surgical work site 200 remains sufficiently irrigated or otherwise covered with water during burring so that the work site 200 and corresponding body tissue does not become overheated to the point of possible injury. Similarly, the flow rates can be controlled or selected to provide sufficient agitation or mixing (e.g., vortex mixing) for pick-up and removal of metal implant particles resulting from burring. Further, the flow rates can be balanced to prevent or reduce flooding of wash fluid out of the surgical site 200 and/or ingress-egress apparatus 100.

In an embodiment, the surgical implant 210 is a mechanical fastening or joining means. For example, implant 210 can be a screw, bolt, prosthesis, TTA cage, or other suitable mechanical fastening or joining means. The implant 210 can be partially or completely attached to or inserted into bone in the surgical subject, for example joining or fastening bones or bone sections together, or joining a bone or bone segment to another prosthetic implant or support device. The implant 210 location in the surgical work site 200 is generally near or adjacent to bones, joints, cartilage, and/or other soft tissue that could be injured by heat and/or (metal) implant 210 particles resulting from burring, if not removed from the surgical work site 200. The surgical implant 210 can include a metal material. The implant 210 is suitably formed from or includes a metallic component or alloy, for example (surgical) stainless steel or other biocompatible metal or metallic alloy.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the apparatus, compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS LIST 100 ingress-egress apparatus
110 inverted frustum surface (e.g., funnel shape or a frustoconical shape)
111 frustum sidewall
112 bottom open area
114 base portion
116 top open area
118 top portion
120 ingress (or inlet) port
122 ingress (or inlet) line
130 egress (or outlet) port
132 egress (or outlet) line
140 handle
150 conforming soft base
160 soft awning (or skirt)
162 soft awning (or skirt) open area/burr access area
200 surgical work site
210 surgical implant
220 surgical burr

What is claimed is:

1. A method for removing a surgical implant, the method comprising:
   providing a surgical subject comprising a surgical implant to be removed, wherein the surgical implant comprises a mechanical fastening or joining means;

providing an ingress-egress apparatus comprising:
an inverted frustum surface comprising a sidewall defining: a bottom open area at a base portion of the frustum surface sidewall, and an opposing top open area at a top portion of the frustum surface sidewall, wherein the top open area has a larger area than the bottom open area;
an ingress port located at the base portion of the frustum surface sidewall and providing fluid communication access from (i) external to the ingress-egress apparatus to (ii) the bottom open area; and
an egress port located at the base portion of the frustum surface sidewall and providing fluid communication access from (i) external to the ingress-egress apparatus to (ii) the bottom open area;
burring the surgical implant with a surgical burr to remove the surgical implant, wherein burring the surgical implant comprises:
providing surgical access to the surgical implant with the ingress-egress apparatus
accessing the surgical implant with the surgical burr through the bottom open area of the ingress-egress apparatus while burring the implant,
irrigating the surgical implant with water delivered through the ingress port of the ingress-egress apparatus, thereby forming a wash fluid comprising the water and burring residue, and
removing the wash fluid through the egress port of the ingress-egress apparatus.

2. The method of claim 1, wherein the ingress-egress apparatus further comprises:
an inlet line in fluid communication with the ingress port; and
an outlet line in fluid communication with the egress port.

3. The method of claim 1, wherein the ingress port and the egress port are spaced apart at an interior location of the bottom open area.

4. The method of claim 1, wherein the ingress-egress apparatus further comprises a conforming soft base attached to the inverted frustum surface at the base portion and around the bottom open area.

5. The method of claim 1, wherein the ingress-egress apparatus further comprises a soft awning cover attached to the inverted frustum surface at the top portion and around the top open area, the soft awning cover defining an interior opening.

6. The method of claim 1, wherein providing surgical access to the surgical implant comprises:
making a surgical opening at a surgical work site where the surgical implant is located in the surgical subject; and
inserting a bottom portion of the ingress-egress apparatus into surgical subject at the surgical work site and positioned above the surgical implant.

7. The method of claim 1, wherein burring the surgical implant comprises partially removing the surgical implant.

8. The method of claim 1, wherein burring the surgical implant comprises completely removing the surgical implant.

9. The method of claim 1, wherein:
irrigating the surgical implant with water comprises injecting the water through the ingress port under pressure to attain a desired wash flow rate and velocity; and
removing the wash fluid comprises applying suction through the egress port.

10. A method for removing a surgical implant, the method comprising:
providing a surgical subject comprising a surgical implant to be removed, wherein the surgical implant comprises a metal material;
providing an ingress-egress apparatus comprising:
an inverted frustum surface comprising a sidewall defining: a bottom open area at a base portion of the frustum surface sidewall, and an opposing top open area at a top portion of the frustum surface sidewall, wherein the top open area has a larger area than the bottom open area:
an ingress port located at the base portion of the frustum surface sidewall and providing fluid communication access from (i) external to the ingress-egress apparatus to (ii) the bottom open area; and
an egress port located at the base portion of the frustum surface sidewall and providing fluid communication access from (i) external to the ingress-egress apparatus to (ii) the bottom open area;
burring the surgical implant with a surgical burr to remove the surgical implant, wherein burring the surgical implant comprises:
providing surgical access to the surgical implant with the ingress-egress apparatus
accessing the surgical implant with the surgical burr through the bottom open area of the ingress-egress apparatus while burring the implant,
irrigating the surgical implant with water delivered through the ingress port of the ingress-egress apparatus, thereby forming a wash fluid comprising the water and burring residue, and
removing the wash fluid through the egress port of the ingress-egress apparatus.

11. The method of claim 10, wherein the ingress-egress apparatus further comprises:
an inlet line in fluid communication with the ingress port; and
an outlet line in fluid communication with the egress port.

12. The method of claim 10, wherein the ingress port and the egress port are spaced apart at an interior location of the bottom open area.

13. The method of claim 10, wherein the ingress-egress apparatus further comprises a conforming soft base attached to the inverted frustum surface at the base portion and around the bottom open area.

14. The method of claim 10, wherein the ingress-egress apparatus further comprises a soft awning cover attached to the inverted frustum surface at the top portion and around the top open area, the soft awning cover defining an interior opening.

15. The method of claim 10, wherein providing surgical access to the surgical implant comprises:
making a surgical opening at a surgical work site where the surgical implant is located in the surgical subject; and
inserting a bottom portion of the ingress-egress apparatus into surgical subject at the surgical work site and positioned above the surgical implant.

16. The method of claim 10, wherein burring the surgical implant comprises partially removing the surgical implant.

17. The method of claim 10, wherein burring the surgical implant comprises completely removing the surgical implant.

18. The method of claim 10, wherein:
- irrigating the surgical implant with water comprises injecting the water through the ingress port under pressure to attain a desired wash flow rate and velocity; and
- removing the wash fluid comprises applying suction through the egress port.

\* \* \* \* \*